United States Patent [19]

Kittelsen et al.

[11] Patent Number: 5,320,114
[45] Date of Patent: Jun. 14, 1994

[54] BOILING AND STABILIZATION TRAY FOR MOUTHGUARDS

[75] Inventors: Jon D. Kittelsen, Fridley; Paul C. Belvedere, Edina, both of Minn.

[73] Assignee: E-Z Gard Industries, Inc., Minneapolis, Minn.

[21] Appl. No.: 67,421

[22] Filed: May 24, 1993

[51] Int. Cl.$^5$ .......................... A61C 5/14; A61C 3/00
[52] U.S. Cl. ......................................... 128/861; 433/6
[58] Field of Search ...................... 128/859–861, 128/62 A; 2/2; 433/213, 214, 6, 37, 46

[56] References Cited

U.S. PATENT DOCUMENTS

| | | | |
|---|---|---|---|
| 257,038 | 4/1882 | McMann | 433/41 |
| 1,117,928 | 11/1914 | Thurmond | 433/46 |
| 1,323,832 | 12/1919 | Chige | 433/46 |
| 1,461,209 | 7/1923 | Bridges | 433/46 |
| 1,470,888 | 10/1923 | Smedley | 433/46 |
| 1,487,392 | 3/1924 | Lee | 433/41 |
| 2,118,980 | 5/1938 | Montgomery | 433/41 |
| 2,630,117 | 3/1953 | Coleman | 128/136 |
| 2,643,652 | 6/1953 | Cathcart | 128/136 |
| 2,694,397 | 11/1954 | Herms | 128/136 |
| 2,750,941 | 6/1956 | Cathcart | 128/136 |
| 2,966,908 | 1/1961 | Cathcart | 128/136 |
| 3,016,052 | 1/1962 | Zubren | 128/136 |
| 3,058,462 | 10/1962 | Greenblum | 128/136 |
| 3,082,765 | 3/1963 | Helmer | 128/136 |
| 3,124,129 | 3/1964 | Grossberg | 128/136 |
| 3,203,417 | 8/1965 | Helmer | 128/136 |
| 3,207,153 | 9/1965 | Goldstein | 128/136 |
| 3,223,085 | 12/1965 | Gores et al. | 128/136 |
| 3,247,844 | 4/1966 | Berghash | 128/136 |
| 3,312,218 | 4/1967 | Jacobs | 128/136 |
| 3,407,809 | 10/1968 | Ross | 128/136 |
| 3,411,501 | 11/1968 | Greenberg | 128/136 |
| 3,448,738 | 6/1969 | Berghash | 128/136 |
| 3,457,916 | 7/1969 | Wolicki | 128/136 |
| 3,485,242 | 12/1969 | Greenberg | 128/136 |
| 3,496,936 | 2/1970 | Gores | 128/136 |
| 3,513,838 | 5/1970 | Foderick et al. | 128/136 |
| 3,518,988 | 7/1970 | Gores | 128/136 |
| 3,682,164 | 8/1972 | Miller | 128/136 |
| 3,692,025 | 9/1972 | Greenberg | 128/136 |
| 3,768,465 | 10/1973 | Helmer | 128/136 |
| 3,864,832 | 2/1975 | Carlson | 32/40 B |
| 3,943,924 | 3/1976 | Kallestad et al. | 128/136 |
| 4,044,762 | 8/1977 | Jacobs | 128/136 |
| 4,063,552 | 12/1977 | Going et al. | 128/136 |
| 4,114,614 | 9/1978 | Kesling | 128/136 |
| 4,185,817 | 1/1980 | Peterson | 272/95 |
| 4,337,765 | 7/1982 | Zimmerman | 128/136 |
| 4,672,959 | 6/1987 | May et al. | 128/136 |
| 4,763,791 | 8/1988 | Halverson | 433/37 |
| 4,791,941 | 12/1988 | Schaefer | 128/136 |
| 4,867,147 | 9/1989 | Davis | 128/859 |
| 4,977,905 | 12/1990 | Kittelsen et al. | 128/861 |
| 5,076,785 | 12/1991 | Tsai | 433/46 |
| 5,152,301 | 10/1992 | Kittelsen et al. | 128/861 |

FOREIGN PATENT DOCUMENTS 480423 8/1929 Fed. Rep. of Germany.

OTHER PUBLICATIONS

American Dental Association. "Give Your Teeth A Sporting Chance." 1985.
Stephen D. Smith, D.M.D. "Muscular Strength Correlated To Jaw Posture and the Temporomandibular Joint." *NYS Dental Journal.* Aug.-Sep. 1978.
W. B. May, D.D.S. "Reduction of Stress in the Chewing Mechanism-Part III." *Basel Facts.* vol. 3, No. 1.

*Primary Examiner*—Michael A. Brown
*Attorney, Agent, or Firm*—Palmatier, Sjoquist & Helget

[57] ABSTRACT

A boiling and stabilization tray has a handle end, shank portion and mouthguard cradle end for supportably receiving and stabilizing a mouthguard for custom fitting. The mouthguard cradle end is connected to the shank opposite the handle end and has a platform for supportably receiving the mouthguard base. An upwardly curved crescent portion engages and supports the anterior and posterior portions of the upward inner lingual wall of the mouthguard. Upwardly curved tabs also extend from the cradle end for engagement with and support of the anterior portion of the upward outer labial wall of the mouthguard. The cradle supports and stabilizes the softened mouthguard during heating, assists in positioning and aligning of the heated mouthguard within the user's mouth, and assists the user in custom fitting of the mouthguard with respect to the user's upper and lower jaw teeth.

7 Claims, 1 Drawing Sheet

BOILING AND STABILIZATION TRAY FOR MOUTHGUARDS

BACKGROUND OF THE INVENTION

The present invention relates generally to protective mouthguards for use in athletics and more particularly, to a boiling and stabilization tray which will assist in heating, positioning and aligning a thermoplastic mouthguard to custom fit a user's mouth.

A number of mouthguards currently exist in the art for protecting the teeth and for reducing the chance of shock, concussions and other injuries as a result of high impact collisions and blows during athletic competition. Mouthguards generally are characterized as being nonpersonalized, universal and stock model type, or are customized to have direct upper jaw tooth-formed contact. Additionally, the mouthguards may be tethered or untethered. Mouthguards that are to be tethered may be fastened to a helmet or face guard to prevent the chance of the mouthguard from being lost as well as to prevent swallowing of the mouthguard or choking on the mouthguard by the user. Custom mouthguards that are personalized for the individual wearer or user may be created by technicians, practitioners or dentists. Alternatively, users, as well as dentists, may create custom fit mouthguards to have direct contact with the teeth, gums and jaws by way of the boil-and-bite method. Ethylene vinyl acetate (EVA) material works suitably well as a thermoplastic material for mouthguards. The EVA mouthguard will readily soften when submerged in boiling water momentarily afterwhich the mouthguard may be removed and fitted about the user's upper jaw, teeth and gums afterwhich the user applies contact pressure as well as suction to custom fit the mouthguard to the upper jaw.

The most common problem with EVA-like material mouthguards that are to be heated and then fitted to the user is that the heated mouthguards become limp and completely lose their shape upon heating. A heated, limp mouthguard is difficult to fit within the user's mouth and quickly form about the user's upper jaw in a timely fashion before the EVA-like material becomes stiff or hard. This problem becomes even more heightened when the particular mouthguard design is further customized to have additional features, such as occlusal pads, or an anterior impact brace which must be properly aligned and positioned.

Further still, dentists, team doctors, practitioners and equipment personnel have had an increasing concern for the temporo mandibular joint (TMJ) and protecting the TMJ from injury. Consequently, the alignment and positioning of the lower jaw and indexing of the lower jaw upon the softened mouthguard to be formed have all recently been receiving additional attention and consideration.

There is a need for a boiling and stabilization tray for use in heating, positioning and aligning thermoplastic mouthguards to custom fit a user's mouth. The tray should receive and support the mouthguard for heating and further permit quick and accurate positioning and aligning of the heated and softened thermoplastic mouthguard to permit custom fitting with respect to all of the above mouthguard features.

SUMMARY OF THE INVENTION

A boiling and stabilization tray has a handle end, shank portion and mouthguard cradle end for supportably receiving and stabilizing a mouthguard for custom fitting. The mouthguard cradle end is connected to the shank opposite the handle end and has a platform for supportably receiving the mouthguard base. An upwardly curved crescent portion engages and supports the anterior and posterior portions of the upward inner lingual wall of the mouthguard. Upwardly curved tabs also extend from the cradle end for engagement with and support of the anterior portion of the upward outer labial wall of the mouthguard. The cradle supports and stabilizes the softened mouthguard during heating, assists in positioning and aligning of the heated mouthguard within the user's mouth, and assists the user in custom fitting of the mouthguard with respect to the user's upper and lower jaw and teeth.

A principal object and advantage of the present invention is that the boiling and stabilization tray supportably receives the mouthguard and continues to support and stabilize the softened mouthguard during heating and positioning to assist the user in custom fitting of the mouthguard to the user's upper jaw teeth.

Another object and advantage of the present invention is that the tray has a upwardly curved crescent portion which engages and supports the anterior and posterior portions of the upward inner lingual wall of the mouthguard and further permits the user to apply pressure with the user's tongue thereat to force the heated upward inner lingual wall of the mouthguard to custom fit to the upper jaw teeth.

Another object and advantage of the present invention is that the tray permits proper alignment and positioning of certain of the mouthguard components as well as permitting the appropriate alignment of the lower jaw to further protect the TMJ.

Another object and advantage of the present invention is that the tray assists in holding the mouthguard during its heating and immediately thereafter for proper fitting of the mouthguard with respect to the upper and lower jaws as well as maintaining the size and shape of the heated, soft, pliable mouthguard.

Another object and advantage of the present invention is that the tray of the present invention permits quick and easy heating and fitting of the mouthguard as heretofore not known.

Other objects and advantages of the present invention will be appreciated upon the reading of the following specification and claims with a study of the attached drawings.

DETAILED SPECIFICATION

Figures 1, 2:
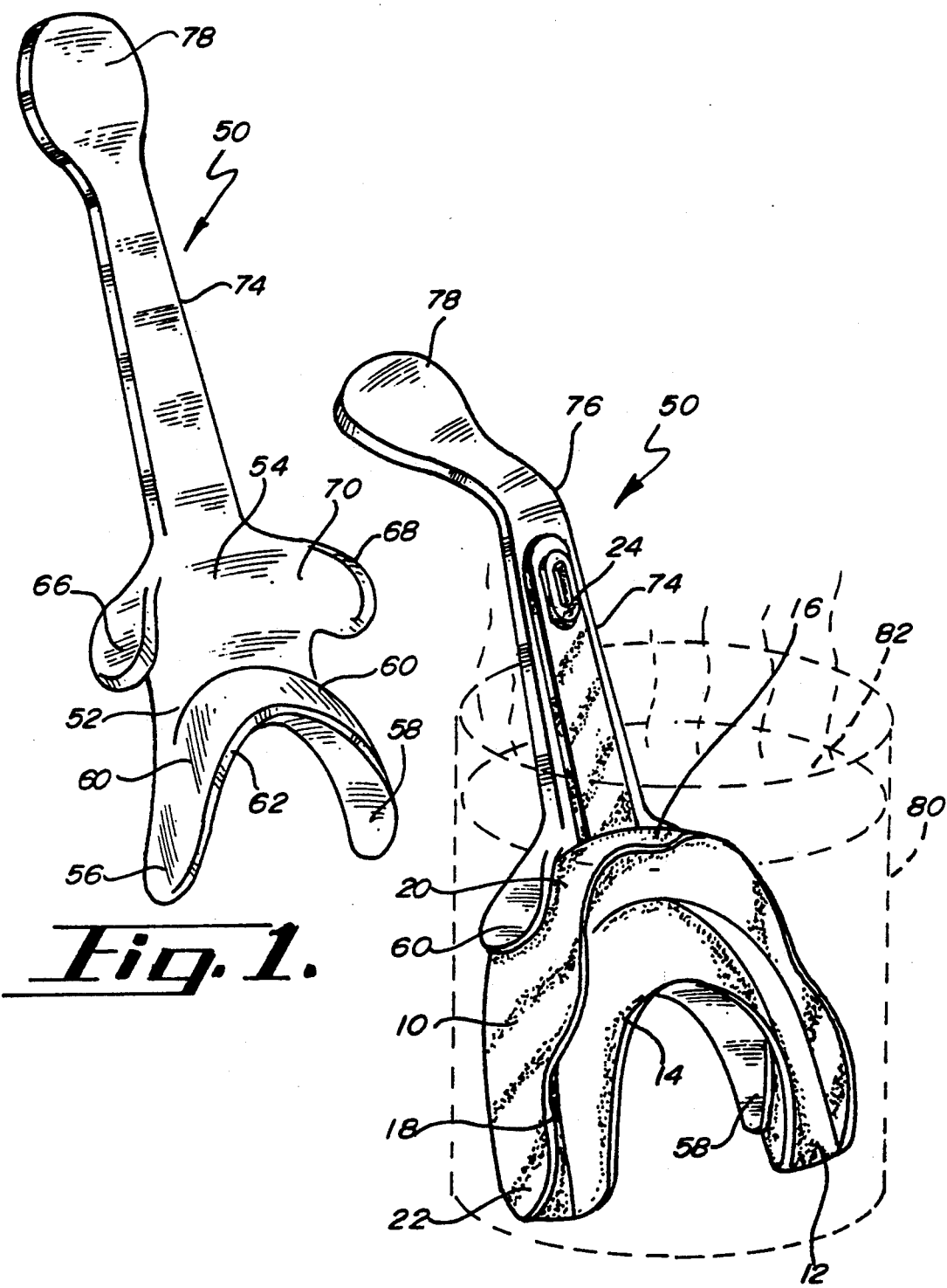
FIG. 1 is a front perspective view of the boiling and stabilization tray of the present invention.
FIG. 2 is a front elevational view of a slightly modified tray supporting a mouthguard in a liquid medium within a container shown in phantom outline.

Referring to the Figures, mouthguard 10 is shown. Mouthguard 10 is intended to be any of the number of mouthguards discussed in the Background with further additional features which the tray 50 of the present invention will permit and facilitate heating and custom fitting. Mouthguard 10 is generally comprised of a U-shaped base 12. From U-shaped base 12 extends an upward inner lingual wall 14 and an upward outer labial wall 16 forming a channel 18 therebetween. Channel 18 receives the teeth of the upper jaw while the bottom of the U-shaped base 12 will permit indexing of the lower jaw. Mouthguard 10 has an anterior portion 20 and posterior portions 22. A tether connecting tab 24 may be optional should the mouthguard 1? be tethered to a helmet or facemask.

The boiling and stabilization tray 50 for mouthguard 10 has a mouthguard cradle or saddle end 52. The cradle 52 has a seat, platform or bed portion 54 which is shaped to readily receive the U-shaped base 12 of an unheated mouthguard 10. Extending upwardly and outwardly in an opposing fashion are legs 56 and 58. Between the substantially flat platform 54 and the upwardly and outwardly extending legs 56 and 58 is an upwardly curved region 60 which makes for a curved, smooth transition and readily supports the softened mouthguard in its ideal condition for fitting. The legs 56 and 58 together with the upwardly curved region 60 together form a smoothly curved crescent or arch portion 62. Opposing the legs 56 and 58 on the cradle 52 are upwardly and outwardly reaching curved arms or tab portions 66 and 68. Tabs 66 and 68 also have upwardly curved portions 70 to readily receive, support and maintain the condition and shape of the softened mouthguard 10.

While the legs 56 or 58 or the crescent portion 62 support the anterior portions 22 of the mouthguard 10, the platform 54 assists in supporting the U-shaped mouthguard base 12 while the tabs 66 and 68 maintain, stabilize and support the upward outer labial wall 16 of the mouthguard 10. By this arrangement, an unsoftened mouthguard may be placed within the cradle 52 and momentarily submerged in boiling water. Upon removal from the water, the cradle 52 and its components support the mouthguard 10 in its original shape, size and condition for easy fitting with the user's mouth.

Shank or elongate intermediate portion 74 extends away from the cradle end 52 and may have an optional bend 76 therein and continuing on to handle end 78. The optional bend 76 advantageously permits the orientation of the hand away from the hot vapors rising upwardly from the container 80 within which is heated or boiling water 82.

The use and advantages may now be more fully appreciated. Initially, the user or individual who is to fit the mouthguard grasps the handle end 78 of the tray 50. With the other hand, the mouthguard 10 is seated within the cradle 52 so that the crescent 62 engages the inner lingual wall 12 of the mouthguard 10 while the tabs 66 and 68 engage the outer labial wall 16 at the anterior portion 20 of the mouthguard 10. Thereafter, the mouthguard 10 is momentarily lowered into boiling water 82 within the container 80.

Next, the tray 50 and mouthguard 10 are removed from the water 82. The user to be fitted with the mouthguard 10 then simply opens his/her mouth and the softened mouthguard 10, in its original shape, size and condition, is positioned within the user's mouth and aligned so that the channel 18 of the mouthguard 10 will receive the upper jaw teeth. The user may then use his/her tongue to apply force along the upwardly curved region 60 of the crescent portion 62 as to force the inner lingual wall 14 to conform to the shape and spacial structure of the upper jaw, teeth and gums. This arrangement will assure a proper fit on the upper jaw as well as a smooth and comfortable surface along the inner lingual wall 14 after the mouthguard has been formed to the user's mouth. Next, the user's lower jaw may be properly aligned with respect to the upper jaw either before or immediately after the tray 50 is slightly lowered away from the mouthguard 10 and removed from the mouth.

The present invention may be embodied in other specific forms without departing from the spirit or essential attributes thereof. Therefor, the illustrated embodiment should be considered in all respects as illustrative and not restrictive, reference being made to the appended claims rather than to the foregoing description to indicate the scope of the invention.

We claim:

1. A boiling and stabilization tray for use in heating, positioning, and aligning a thermal plastic mouthguard to custom fit to a user's mouth, the mouthguard having an U-shaped base, with upward inner lingual and outer labial walls extending from the U-shaped base forming a channel for upper jaw teeth and having posterior and anterior portions, the tray comprising:
   (a) a handle end for gripping and orienting the tray;
   (b) a shank portion extending away from the handle portion; and
   (c) a mouthguard cradle end connected to the shank opposite the handle end, the cradle end having a platform for supportably receiving the mouthguard base with an upwardly curved crescent portion comprising opposing upwardly and outwardly curved legs opposite the handle end for engagement with and support of the anterior and posterior portions of the upward inner lingual wall of the mouthguard and a pair of opposing upwardly curved tab portions for engagement with and support of the anterior portion of the upward outer labial wall, the cradle being adapted to support and stabilize the softened mouthguard during heating, to assist in positioning and aligning the heated mouthguard within the user's mouth, and to assist the user in custom fitting the mouthguard to the user's upper jaw teeth.

2. The tray of claim 1, wherein the platform extends outwardly to smoothly join the crescent portion to form an upwardly curved region between the platform and the crescent portion whereat the user may apply pressure with the user's tongue to force the heated inner lingual wall of the mouthguard to custom fit to the upper jaw teeth.

3. The tray of claim 1, wherein the handle end is in-line with the shank.

4. The tray of claim 1, wherein the handle end is offset from the shank to avoid rising burning vapors.

5. The tray of claim 1, wherein the tray is made from a plastic that will not soften when the mouthguard is heated.

6. The tray of claim 5, wherein the plastic is chosen from a group consisting of polystyrene, nylon and thermoplastic rubber.

7. A boiling and stabilization tray for use in heating, positioning, and aligning a thermal plastic mouthguard to custom fit to a user's mouth, the mouthguard having an U-shaped base, with upward inner lingual and outer labial walls extending from the U-shaped base forming a channel for upper jaw teeth and having posterior and anterior portions, the tray comprising:
   (a) a handle end for gripping and orienting the tray;
   (b) a shank portion extending away from the handle portion; and
   (c) a mouthguard cradle end connected to the shank opposite the handle end, the cradle end having a platform for supportably receiving the mouthguard base with an upwardly curved crescent portion comprising opposing upwardly and outwardly curved legs opposite the handle end for engagement with and support of the anterior and posterior portions of the upward inner lingual wall of the mouthguard wherein the platform extends outwardly to smoothly joint he crescent portion to form an upwardly curved region between the platform and the crescent portion whereat the user may apply pressure with the user's tongue to force the heated inner lingual wall of the mouthguard to custom fit to the upper jaw teeth, and a pair of opposing upwardly curved tab portions for engagement with and support of the anterior portion of the upward outer labial wall to support and stabilize the softened mouthguard during heating, to assist in positioning and aligning the heated mouthguard within the user's mouth, and to assist the user in custom fitting the mouthguard to the user's upper jaw teeth.

* * * * *

UNITED STATES PATENT AND TRADEMARK OFFICE
CERTIFICATE OF CORRECTION

PATENT NO. : 5,320,114

DATED : June 14, 1994

INVENTOR(S) : Jon D. Kittelsen, Paul C. Belvedere

It is certified that error appears in the above-identified patent and that said Letters Patent is hereby corrected as shown below:

In column 3, line 4, after the word "mouthguard", please delete "1?" and replace with the numeral --10--.

In column 5, line 7, after the word "smoothly", please delete "joint he" and replace with --join the--.

Signed and Sealed this

Sixth Day of September, 1994

Attest:

BRUCE LEHMAN

*Attesting Officer*  Commissioner of Patents and Trademarks